United States Patent
Yoon

(10) Patent No.: US 7,624,454 B2
(45) Date of Patent: Dec. 1, 2009

(54) HAND-PACKING INSTRUMENT IN THE FORM OF GLOVES

(75) Inventor: Seongjun Yoon, Seoul (KR)

(73) Assignee: iNtRON Biotechnology Inc. (KR)

( * ) Notice: Subject to any disclaimer, the term of this patent is extended or adjusted under 35 U.S.C. 154(b) by 0 days.

(21) Appl. No.: 11/517,088

(22) Filed: Sep. 7, 2006

(65) Prior Publication Data

US 2007/0124847 A1 Jun. 7, 2007

(30) Foreign Application Priority Data

Dec. 5, 2005 (KR) ................. 20-2005-0034225 U

(51) Int. Cl.
*A41D 19/01* (2006.01)

(52) U.S. Cl. .................. 2/158; 2/159; 2/164; 424/402; 15/227; 601/21

(58) Field of Classification Search ............... 2/158, 2/159, 164; 424/402; 15/227; 601/21, 22
See application file for complete search history.

(56) References Cited

U.S. PATENT DOCUMENTS

| | | | | |
|---|---|---|---|---|
| 1,817,385 A * | 8/1931 | Marks | ............................. | 2/158 |
| 2,609,543 A * | 9/1952 | Farrell | ............................. | 2/158 |
| 4,185,330 A * | 1/1980 | Stager | ............................. | 2/164 |
| 4,186,445 A * | 2/1980 | Stager | ............................. | 2/164 |
| 5,050,596 A * | 9/1991 | Walasek et al. | ............. | 607/111 |
| 5,720,047 A * | 2/1998 | Spitzer | ........................ | 2/161.1 |
| 6,141,801 A * | 11/2000 | Helenick | ........................ | 2/159 |
| 6,692,756 B2 * | 2/2004 | Chou | ........................ | 424/402 |
| 7,043,768 B2 * | 5/2006 | Gogarty | ..................... | 2/161.6 |

FOREIGN PATENT DOCUMENTS

| KR | 0270904 | 4/2002 |
|---|---|---|
| KR | 0397459 | 9/2005 |

* cited by examiner

*Primary Examiner*—Gary L Welch
*Assistant Examiner*—Alissa J Tompkins
(74) *Attorney, Agent, or Firm*—Ballard Spahr LLP

(57) ABSTRACT

Disclosed is a hand-packing instrument in a mitten shape or a glove shape for caring for skin of the back of the hand. The hand-packing instrument has a mitten shape or a glove shape comprising two sheets overlapped and seamed at their edges, in which the two sheets make a mitten shape having an opening through which a hand can be inserted, a first insertion part for enclosing a thumb and a second insertion part for enclosing the four fingers other than the thumb, and an absorbent attached to the inner surface of one of the sheets.

1 Claim, 6 Drawing Sheets

HAND-PACKING INSTRUMENT IN THE FORM OF GLOVES

BACKGROUND OF THE INVENTION

1. Field of the Invention

The present invention relates, in general, to a hand packing instrument, and, more particularly, to a hand packing instrument having a mitten form or a glove form and being capable of promoting healthy skin of the back of the hand.

2. Description of the Related Art

Recently, women generally care for their skin by moisturizing and supplying nutrients to their skin through a method of applying a mask pack comprising a poultice layer containing cosmetic material and moisturizer and a base layer on their faces for a predetermined time and removing the mask pack after the time has elapsed.

Mask packs have been used for caring for face skin so far but recently they are beginning to be used for caring for skin elsewhere on the body, exposed to the outdoors, particularly neck skin. Accordingly, neck packs for neck skin use have been commercialized, so that the requirement to promote healthy neck skin and eliminate neck wrinkles in women has been satisfied.

The above described packs and skin care instruments, are developed for caring for relatively soft skin such as face skin or neck skin. Accordingly, there is still a need for a skin care instrument for caring for relatively rough skin such as hand skin.

SUMMARY OF THE INVENTION

Accordingly, the present invention has been made keeping in mind the above problems occurring in the related art, and an object of the present invention is to provide a hand-packing instrument in mitten form or glove form, capable of promoting smooth, clean and healthy hand skin by supplying moisture and nutrients to hand skin, and particularly to skin on the back of the hand.

In order to achieve the above object, according to one aspect of the present invention, there is provided a hand-packing instrument comprising two sheets seamed at edges other than a hand insertion opening, the two sheets having a first insertion part for receiving a thumb therein and a second insertion part for receiving the four fingers other than the thumb, and an absorbent provided on the inner surface of the sheets. The second insertion part can be divided into four insertion holes, so that the four fingers can be respectively inserted through the four insertion parts, and the hand-packing instrument has a glove shape. The absorbent capable of absorbing a variety of cosmetic materials for improving the state of health of the skin may be made of a piece of unwoven fabric or cotton fabric. The hand-packing instrument may further comprise an opening and closing member, so that the hand-packing instrument has a sealed inner space therein when the opening and closing part is closed. A skin care material can be added to the absorbent after a user puts on the hand-packing instrument instead of the skin care material being (?) applied to the absorbent before a user puts on the hand-packing instrument. The sheets for the hand-packing instrument may be made of transparent or half-transparent vinyl or silver clad vinyl.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
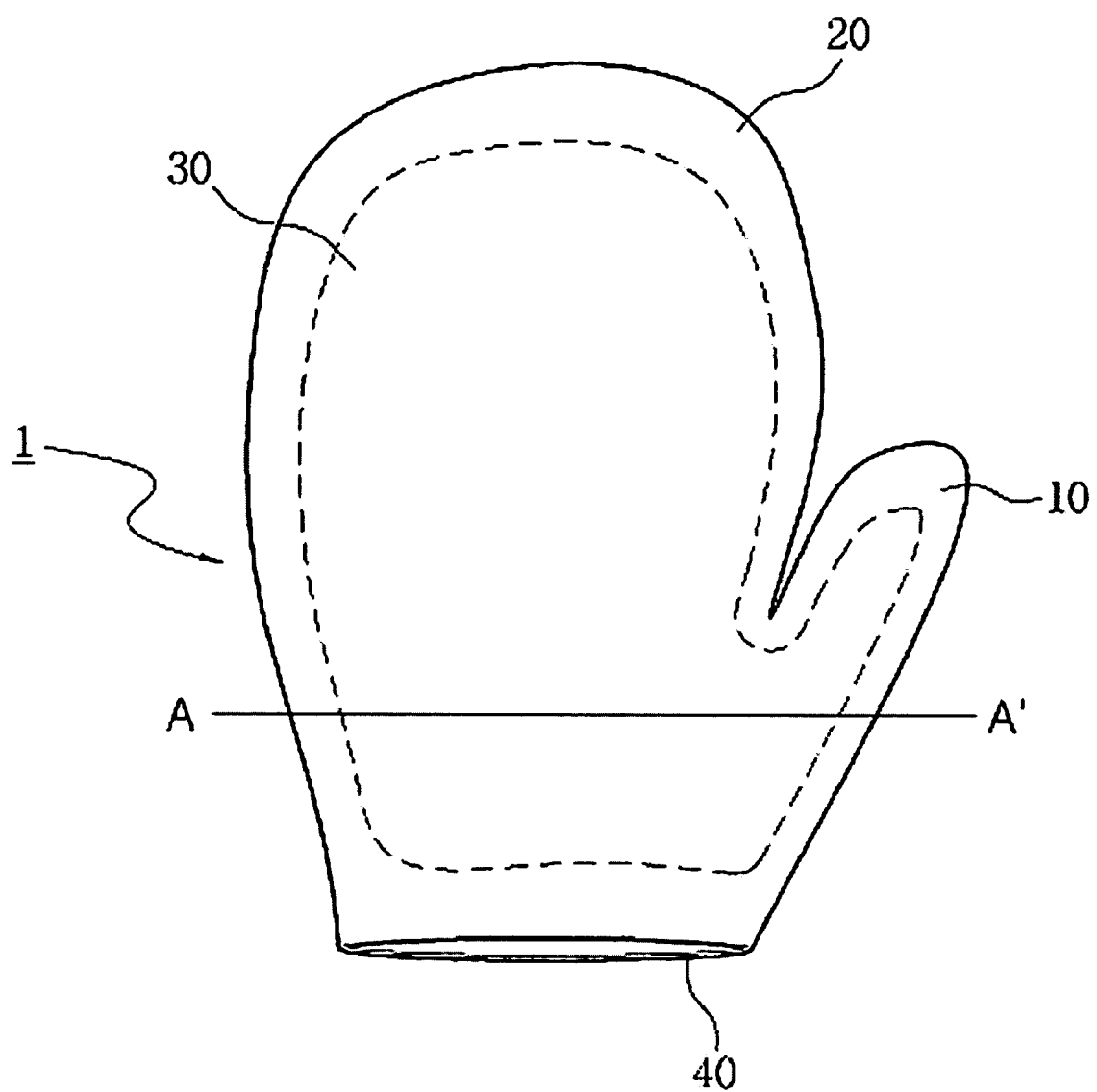
FIG. 1 is a schematic view illustrating a hand-packing instrument in a mitten form, in accordance with a first embodiment of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 2:
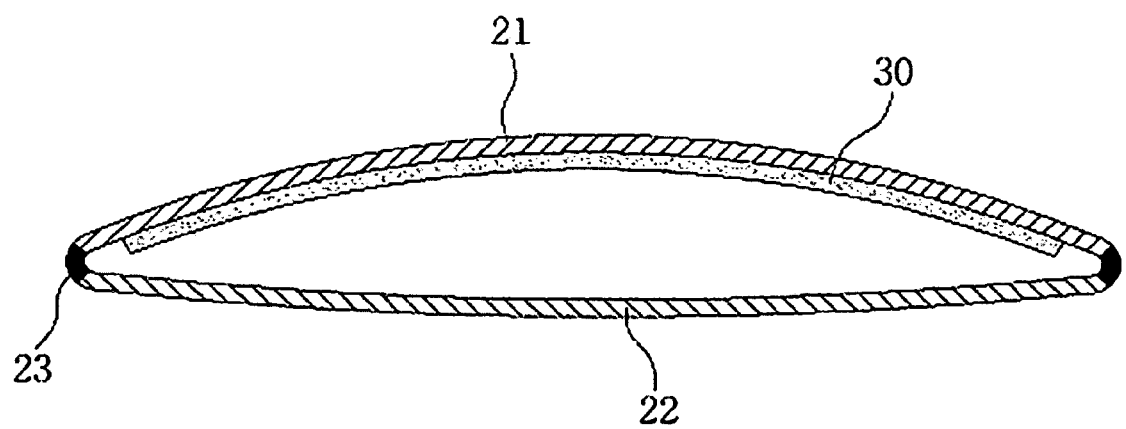
FIG. 2 is a sectional view taken along the line A-A in FIG. 1.

FIG. 1 illustrates a hand-packing instrument for a right hand according to one embodiment of the present invention. Referring to FIG. 1, the hand-packing instrument in a mitten form includes a first insertion part 10 and a second insertion part 20, and has an opening 40 at a portion extending from the first insertion part 10 and the second insertion part 20. The opening 40 is a hole through which a hand can be inserted into the hand-packing instrument having a mitten shape or a glove shape. The first insertion part 10 encloses a thumb and the second insertion part 20 encloses the four fingers other than the thumb. An absorbent 30 having a curved shape similar to the whole outer contour of the first part 10 and the second part 20 is attached to the inner upper surface of the hand-packing instrument. The absorbent can absorb cosmetic material serving as a skin care ingredient and moisturizer, and the shape of the absorbent is not limited to the shape shown in FIG. 1. FIG. 2 illustrates a section of the hand-packing instrument, taken along the line A-A.

Figure 3:
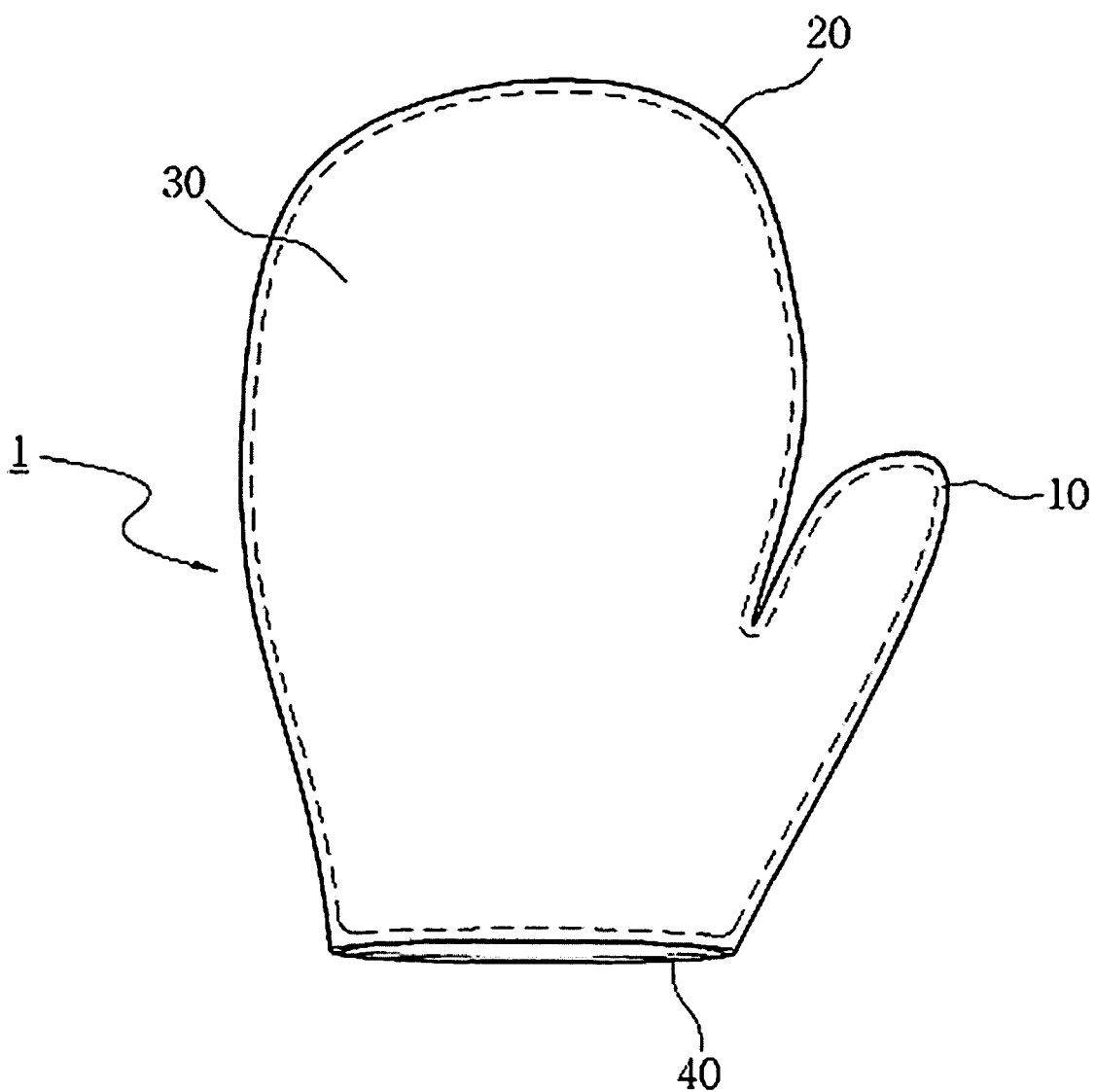
FIG. 3 is a schematic view illustrating a hand-packing instrument in a mitten form, in accordance with a second embodiment of the present invention.
Figure 4:
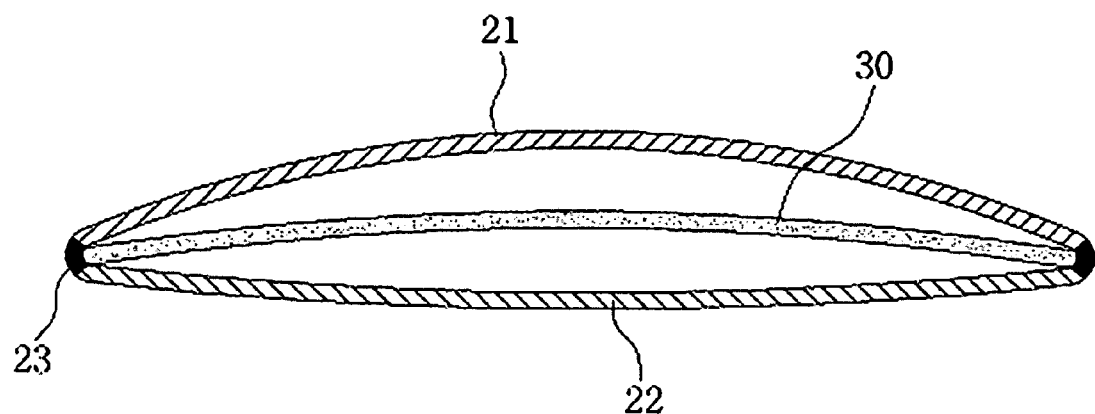
FIG. 4 is a sectional view taken along the line B-B in FIG. 3.

The hand-packing instrument illustrated in FIG. 1 and FIG. 2 is for a right hand and has the absorbent 30 attached to the inner upper surface thereof, but the hand-packing instrument according to the present invention is not limited thereto. As shown in FIG. 3 and FIG. 4, the absorbent 30 is not attached to the inner surface. That is, it can have the same shape as upper and lower sheets which constitute a glove or a mitten of the hand-packing instrument, and it is seamed or bonded together with the sheets along their edges. The absorbent is not attached to an inner surface of the mitten or the glove made by the two sheets but is fixed at a sealing part of the mitten or the glove, so that the absorbent is disposed in the inner space of the mitten or the glove made by bonding the edges of the two sheets. Accordingly, the hand-packing instrument according to this embodiment can be used for either the right hand or the left hand. The absorbent is made of unwoven fabric or cotton fabric.

Figure 5:
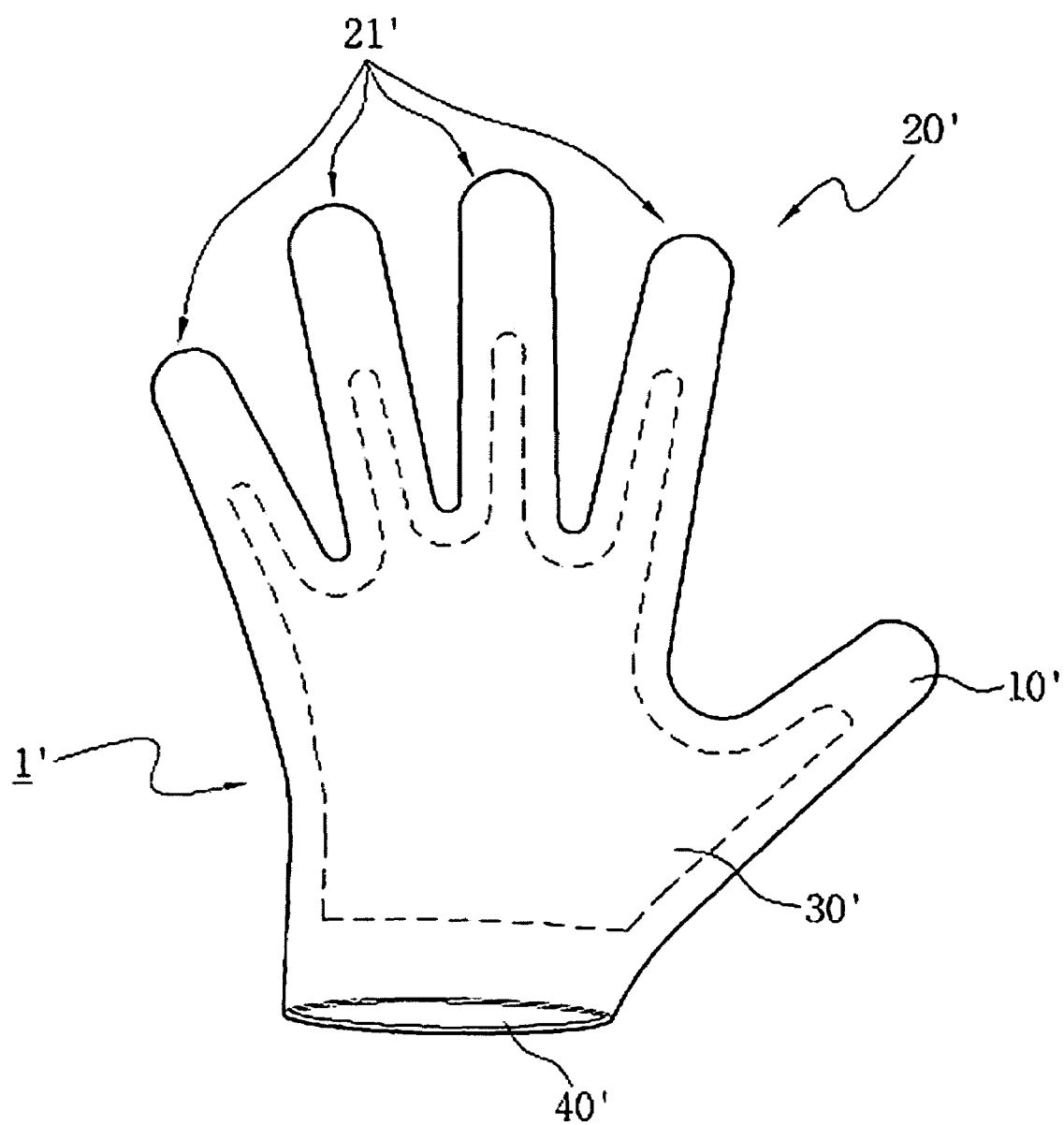
FIG. 5 is a schematic view illustrating a hand-packing instrument in a glove form, in accordance with a third embodiment of the present invention.

FIG. 5 illustrates a hand-packing instrument 1' according to a third embodiment of the present invention. The hand-packing instrument according to this embodiment has five fingers, that is, it has a glove shape. The hand-packing instrument 1' with five fingers comprises a first insertion part 10' and a second insertion part 20', and the second insertion part 20' comprises four insertion holes 21' for enclosing respective four fingers therein other than a thumb. The hand-packing instrument 1' further comprises an absorbent 30' having a curved outer contour similar to the shape of the whole outer contour of the first insertion part 10' and the insertion holes 21'. The absorbent 30' is attached to the inner upper surface of the hand-packing instrument. The absorbent 30' can be added or impregnated with cosmetic material having skin care effect and moisturizer.

Figure 6:
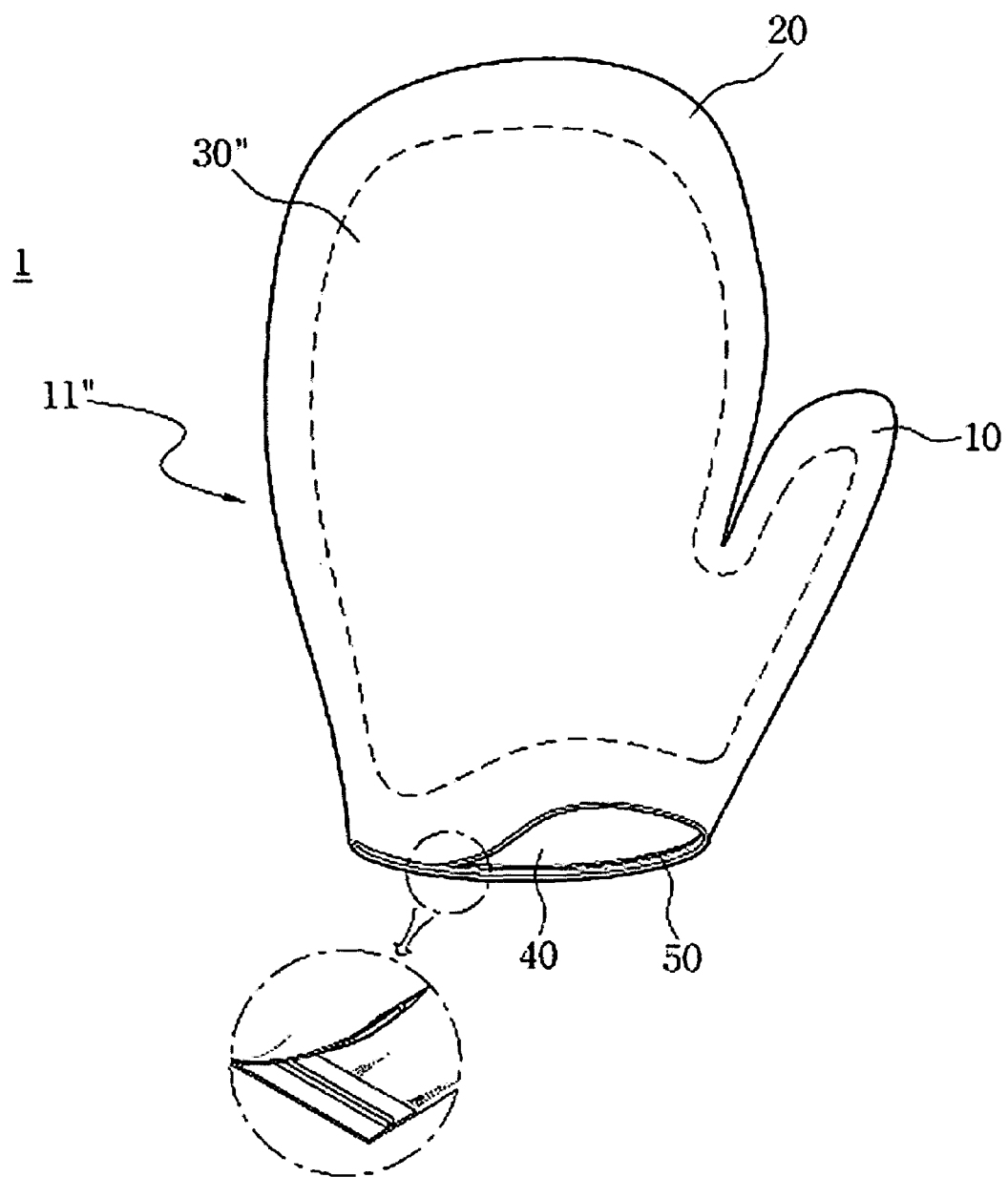
FIG. 6 is a view illustrating a hand-packing instrument in a mitten shape having an opening and closing means according to a fourth embodiment of the present invention.

FIG. 6 illustrates a hand-packing instrument for the right hand in the form of a mitten, according to a further embodiment of the present invention. The hand-packing instrument according to this embodiment has an opening and closing means at an opening portion thereof. Referring to FIG. 6, the hand-packing instrument 1 in the form of a mitten comprises a first insertion part 10 for enclosing a thumb and a second insertion part 20 for enclosing the other four fingers, and has an opening 40 through which a hand can be inserted into the hand-packing instrument in a mitten form, at a portion extended from the first insertion part 10 and the second insertion part 20. On the surfaces of the mitten near the opening 40, zipper clips 50 are provided to the surfaces facing each other, thereby opening and closing the hand-packing. On the inner upper surfaces of the first insertion part 10 and the second insertion part 20, an absorbent 30" having a curved shape similar to the shapes of the insertion parts 10 and 20 is attached. The absorbent 30" need not contain any cosmetic material or moisturizer therein. When using the hand-packing instrument with the zipper clips, a user can supply cosmetic material desired by the user into the absorbent 30". That is, this hand-packing instrument is a user friendly product. The zipper clips are exemplified as an example of the opening and closing means, but general opening and closing means such as an attachment member or a string can be used.

A method of manufacturing the hand-packing instrument in a mitten form or a glove form is described with reference to FIG. 2 and FIG. 4. First, two vinyl sheets 21 and 22 having an outer contour of a mitten or a glove are prepared. A piece of unwoven fabric 20 is attached to the surface of the vinyl sheet 21. The vinyl sheets 21 and 22 are fully overlapped in a manner such that the unwoven fabric 30 is disposed between the vinyl sheet 20 and the vinyl sheet 21. Edges 23 of the vinyl sheets 20 and 21 except for a portion serving as the opening through which a hand is inserted are bonded through a high frequency bonding method, thereby completing formation of the hand-packing instrument in a mitten form or a glove form. On the other hand, in the case of the hand-packing instrument for both hands shown in FIG. 4, two vinyl sheets 21 and 22 having a mitten or a glove shape, and a piece of unwoven fabric having the same shape of the two vinyl sheets 21 and 22 are prepared, and then are overlapped in a manner such that the unwoven fabric 30 is disposed between the two vinyl sheets 21 and 22. Then, edges of the overlapped structure except for the portion serving as the opening through which the hand is inserted are bonded through a high frequency bonding process using a bonding machine. Here, the bonded edges are called a sealing part 23. The unwoven fabric 30 is not attached to the vinyl sheets 21 and 22 but is fixed only at the sealing part 23. Accordingly, the hand-packing instrument according to this embodiment can be used for either the right hand or the left hand.

The above described embodiments are preferred examples of the hand-packing instrument according to the present invention, but the present invention does not exclude a variety of variations and modifications that can be derived from the embodiments. For example, the hand-packing instrument may be prepared as it is sealed without an opening through which a user's hand can be inserted, so that the opening of the completely sealed hand-packing instrument must be formed by a user on the spot when using it. The configuration of the hand-packing instrument according to embodiments of the present invention is the finally completed form when it is used. Accordingly, the hand-packing instruments can be manufactured and sold as they are sealed, that is, without openings.

The hand-packing instrument in a mitten form or a glove form used for skin care has the following advantages.

A user can easily and simply care for hand skin merely by wearing the hand-packing instrument like a mitten or a glove when a user wants the skin of the back of the hand to be treated. A user can achieve the skin care effect of the back of the hand without exposing the skin to be cared for outside. A user can work using his or hands even while caring for hand skin because the hand-packing instrument is in a mitten or a glove form. A user can enjoy the relatively improved skin care effect due to a warming effect which can be achieved since the hand-packing instrument can be sealed using the opening and closing means.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A hand-packing instrument in a mitten shape or a glove shape for skin care of the back of a hand comprising:
   two sheets overlapping and seamed at their edges, in which the two sheets form a mitten shape having an opening through which a hand can be inserted, a first insertion part for enclosing a thumb and a second insertion part for enclosing four fingers other than the thumb, wherein a sealing part to bond the two sheets to each other is formed at the edges of the sheets; and
   only one absorbent fixed to the sealing part only and not attached to either inner surface of the two sheets, such that the absorbent is capable of being held on the back of either a right or left hand inserted within the opening between the absorbent and either one of the two sheets within the opening.

* * * * *